US011118229B2

(12) United States Patent
Borgio et al.

(10) Patent No.: US 11,118,229 B2
(45) Date of Patent: Sep. 14, 2021

(54) SINGLE TUBE MULTIPLEX PCR METHOD FOR THE DETECTION OF HBA1, HBA2 AND HBA12 GENES

(71) Applicant: Imam Abdulrahman Bin Faisal University, Dammam (SA)

(72) Inventors: J. Francis Borgio, Dammam (SA); Sayed Abdulazeez, Dammam (SA); Fahd A. Al-Muhanna, Dammam (SA); Amein Kadhem Al-Ali, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 237 days.

(21) Appl. No.: 16/257,195

(22) Filed: Jan. 25, 2019

(65) Prior Publication Data
US 2020/0239956 A1 Jul. 30, 2020

(51) Int. Cl.
*C12Q 1/6883* (2018.01)
*C12Q 1/686* (2018.01)
*C12Q 1/6806* (2018.01)

(52) U.S. Cl.
CPC ........... *C12Q 1/6883* (2013.01); *C12Q 1/686* (2013.01); *C12Q 1/6806* (2013.01); *C12Q 2600/16* (2013.01)

(58) Field of Classification Search
None
See application file for complete search history.

(56) References Cited

U.S. PATENT DOCUMENTS

2005/0239069 A1   10/2005   Maurer et al.

FOREIGN PATENT DOCUMENTS

| CN | 1626671 A | 6/2005 |
| CN | 103421903 B | 2/2015 |
| CN | 105861661 A | 8/2016 |
| CN | 104894279 B | 10/2016 |
| CN | 106399478 A | 2/2017 |
| CN | 106636344 A * | 5/2017 |

OTHER PUBLICATIONS

Uchida, Gene Expression Profiling for Biomarker Discovery. In: Appasani, K. Southern E.M. (eds) Bioarrays, Humana Press, 2007. (Year: 2007).*
Traeger-Synodinos, et al. ; EMQN Best Practice Guidelines for molecular and haematology methods for carrier identification and prenatal diagnosis of the haemoglobinopathies ; European Journal of Human Genetics 23 ; pp. 426-437 ; Jul. 23, 2014 ; 12 Pages.
Mo ZP, et al. ; Detection of αglobin gene deletion and duplication using quantitative multiplex PCR of short fluorescent fragments. ; Clin Chem Lab Med 50 (4) ; pp. 649-654 ; Dec. 17, 2011 ; Abstract Only ; 1 Page.
Pornprasert, et al. ; Detection of α-thalassemia-1 Southeast Asian and Thai Type Deletions and β-Thalassemia 3.5-kb Deletion by Single-tube Multiplex Real-time PCR with SYBR Green1 and High-resolution Melting Analysis ; Korean J Lab Med 31 ; pp. 138-142 ; Mar. 25, 2011 ; 5Pages.
Koren, et al. ; Response to hydroxyurea therapy in b-thalassemia ; American Journal of Hematology ; pp. 366-370 ; 2008 ; 5 Pages.
Borgio, et al. ; A novel HBA2 gene conversion in cis or trans: "α12 allele" in a Saudi population ; Blood Cells, Molecules and Diseases 53 ; pp. 199-203 ; Jul. 25, 2014 ; 6 Pages.
Borgio ; Molecular nature of alpha-gobin genes in the Saudi population ; Med J vol. 36 (11) ; 2015 ; 6 Pages.

* cited by examiner

*Primary Examiner* — Angela M. Bertagna
*Assistant Examiner* — Carolyn L Greene
(74) *Attorney, Agent, or Firm* — Oblon, McClelland, Maier & Neustadt, L.L.P.

(57) ABSTRACT

One aspect of the invention is a method for amplifying alpha globin genes HBA1, HBA2 and HBA12 in a single PCR tube to determine an HBA genotype of a subject. This method employs five primers selected to accurate and sensitively identify the HBA1, HBA2, and HBA12, a gene found at a higher frequency in citizens of Saudi Arabia, by accurately annealing to nucleic acids in a biological sample and simultaneously amplifying sequences encoding the alpha globin genes. This invention includes a procedure and required reagents for the amplification of alpha globin genes in a single PCR tube.

20 Claims, 8 Drawing Sheets

Specification includes a Sequence Listing.

FIG. 2

| Name of the gene | Forward/ Reverse primers | Sequence (5'>3') | Melting temperature | Amplicon (bp) |
|---|---|---|---|---|
| HBA2 | Forward (MA2F) | TCTCCCCTGTCCTTTCCCTACCCAGAGC (SEQ ID NO: 3) | 70.07 | 1874 |
| | Reverse (MA2R) | CTCCCTGCAGTTCTCCCTCCCCAGC (SEQ ID NO: 4) | 70.11 | |
| HBA12 | Forward (MA12F) | GCCCTCGGCCCCACTGACCCTCTT (SEQ ID NO: 5) | 72.06 | 396 |
| | Reverse (MA2R) | CTCCCTGCAGTTCTCCCTCCCCAGC (SEQ ID NO: 6) | 70.11 | |
| HBA1 | Forward (MA1F) | TGTTTATTCCTTCCCGGTGCCTGTCACTCAA (SEQ ID NO: 1) | 69.32 | 1231 |
| | Reverse (MA12R) | AGGGTCAGTGGGGCCGAGGGCCCAGG (SEQ ID NO: 2) | 76.86 | |

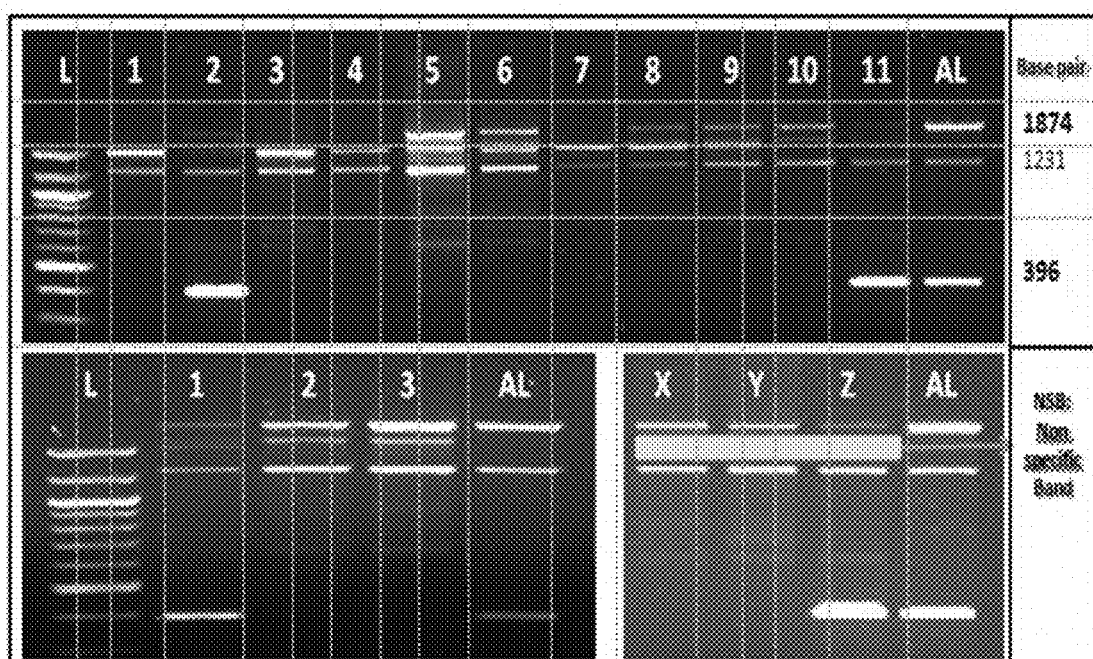

FIG. 6

>HBA2 sequence 1874bp tctccctgtcctttcctacccagagccaagttgtttatctgtttacaaccagtatttacctagcaagtcttccatcagatagcatttggagagctggggtgtaacagtgaaccacgacctctaggccagtgggagag
tcagtcacacaaactgtgagtccatgacttggggcttagccagccactaaccaccacgcgccacccaacaaccccgggtagaggagtctgaatctggagccgaccccaagccagccaccgtgcttttgcgtcct
ggtgtttgttccttccccggtgctgtaactcaagcacactagtgactatcgccagagggggaaagggagctgcaggaagcgaggctggagagcaggaggggctctgcgcagaaattctttgagttcctatggagccag
ggcgtccgggtgcgcgcattcctctccgcccaaggattgggcgaagccctccggctcgcactcgctcgccgtcgtgtccccgatccgctcggtcgatgtcgcgctccagcgcgtgccaggccgggggaggg
tgcgggctgactttctccctccgctaggggacgctccggcgcccgaaggaaagggtggcgctgcgctccggggtgcacgagccgacagccgcgaccccsacgggccggccccgccagcgccgctaccgcc
ctgccccgggcgagcgggatgggccgggagtggagtggccgggtggaggggtggagacgtcctggcccccgcccgcgtgcacccccaggggaggccgagccgccgccggccccgcgcaggcccgc
ccgggactccctgccgtccaggcgcgtgcgccgggctccgcgccagccatgagcgccgccggccgggtgtgccccgcgcgccaagcatcaaacctggccgctgccgctcggggccggacttcttggcc
ccacagactcagagagaaccccaccatggtgctgtctcctgccgacaagaccaacgtcaaggccgctggggtaaggtcggcgcgcacgctggcgagtatggtgcggaggccctggagaggtgaggctccctc
cctgctccgaccgggctcctcgccgccggaccacaggccaccctcaacgtcatggcccggaccaaaccccaccccactctgcttctcccgcaggatgttcctgtccttccccaccaccaagacc
tactttccccgcacttcgacctgagccacggctctgccccaggttaagggccacggcaagaaggtggccgacgcgctgaccaacgccgtggcgcacgtggacgacatgcccaacgccgtgtccgcctgagcgac
ctgcacgcgcacaagcttcgggtggaacccggccactttaaggtgagcggcggcggccgggaagcgtctgggctgagggcgagatgggcgcttctctcagggcagaggatcacgcgggttgcgggaggtgt
agcgcaggcggcggctgggcctgggccgcactgaacctttctctgcacagctcctaagcactgctgctggtgacctggccgccaactcccgcgcgagttaaccctgcggtgcacgctctcctggac
aagtttccttggctctgtgagcacgtgctgacctccaaataccgttaagtggagcctggttagccgttcctctgccgcgtgggcctcccaacgggccctctccctcctccttgcacgagcctctggtctggctttgaata
aagtctgagtgggcagccagcctgtgtgtgcctgggtctctctatccggaatgtgccaacatggaggtgtttctgtctcagaccaaggacctctgcagctgcatggggctgggggaggagaactgcaggg
ag

FIG. 7

>HBA12 sequence 396bp gcctctggaccaactgacccttctctgcacagtcctaagcaactgcctgctgg[g]gacctggncgtcraccttcctgnugagttcaccntgcggtgcacgcctccctggacaagttcctggcttctgtgagcaccgtgctgactccaactacggttaag ctggagcctcggtagccgttcctnctgccngctgggcctnccaaggggcctcctcacctccttgcacnggccnttcctgghctttgaataaagtctgagtgggcagcagcctgtgctgcctggctctcctatcccggaatgtgcaacaatgggggtgttttacctgtc taagaccaaggaccttctctgcagcctgcatgggtgtggggaggagaaatgcagggag

FIG. 8

>HBA1 sequence 1231bp tgtttattccttcccggtgcctgtcactcaagcacactagtgactatcgccgagggaaaggagagctgcaggaagcgaggctggagagcaggagggctctgcgcagaaattctttgagttcctatgggcaggg
cgtccgggtgcgcgcattccttctcccgcgcccaggattgggcgaagcctcccggctcgcactcgctcgccgtgtgttcccccgatcccgctggagtcgatgcgcgtccagcgcgtgcaggccggggcgaggtg
cgggctgactttctccctcgctagggacgctccggcgtccgaaaggaaaggggtgggcgtcgctccgggtgcacgagccgacagcgccgacccctcaacgggcggccccgcagcgccgctaccgcccct
gccccgggcgagcgggatggcgggtgaggtggcgggtggagtggagtgagtggaccgtccggccccgcccgcgtgcaccccaggggaggccgagccgccgccggcccgcgcaggccccgcc
cgggactccctgcggtccaggccgcgccccgggctccgcgcaagccaatgagccgcgccccggccgggcgtgccccgcgccccaagcataaacctggcgcgctcgcggccggcactcttctggtcccc
acagactcagagagaaccccatcatggtgctgtctcctgccgacaagaccaacgtcaaggccgcctggggtaagctcggcgcgcacgctggcgagtatggcgccgaggccctgaggagtgaggctccctccc
ctgctccgaccccggctcctcgccgcccggaccacaggccatcccctcaacgtcctggccccggacctgaaccccaccctcactctgcttctcccgccaggatgttcctgtccttccccaccaccaagaccta
cttccgcacttcgacctgagccacggctctgcccaggttaagggccatcggcaagaaggtggccgacgcgctgaccaacgccgtggccgcacgtgacgacatgcccaacgccgtcgccctgagcgatct
gcacgcgcacaagcttcgggtggaccggtcaacttcaaggtgagcggcgggccgagaagcgatctgggtcgaggagcgagatggcgcttcctgcagggcagaggatcacgcaggttgcggaggtgta
gcgcaggcggcggctgcggacctggagcctggccccactgacc

SEQUENCE LISTING

<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Primer MA12F

<400> SEQUENCE: 1
gccctcggcc ccactgaccc tctt                                      24

<210> SEQ ID NO 2
<211> LENGTH: 25
<212> TYPE: DNA
<213> ORGANISM: Artificial Sequence
<220> FEATURE:
<223> OTHER INFORMATION: Primer MA2R

<400> SEQUENCE: 2
ctccctgcag ttctccctcc ccagc                                     25

<210> SEQ ID NO 3
<211> LENGTH: 31
<212> TYPE: DNA
<213> ORGANISM: Artificial Sequence
<220> FEATURE:
<223> OTHER INFORMATION: Primer MA1F

<400> SEQUENCE: 3
tgtttattcc ttcccggtgc ctgtcactca a                              31

-continued

<210> SEQ ID NO 4
<211> LENGTH: 26
<212> TYPE: DNA
<213> ORGANISM: Artificial Sequence
<220> FEATURE:
<223> OTHER INFORMATION: Primer MA12R

<400> SEQUENCE: 4
agggtcagtg gggccgaggg cccagg                                          26

<210> SEQ ID NO 5
<211> LENGTH: 28
<212> TYPE: DNA
<213> ORGANISM: Artificial Sequence
<220> FEATURE:
<223> OTHER INFORMATION: Primer MA2F

<400> SEQUENCE: 5
tctcccctgt cctttcccta cccagagc                                        28

<210> SEQ ID NO 6
<211> LENGTH: 25
<212> TYPE: DNA
<213> ORGANISM: Artificial Sequence
<220> FEATURE:
<223> OTHER INFORMATION: Primer MA2R (same as SEQ ID NO: 2)

<400> SEQUENCE: 6
ctccctgcag ttctccctcc ccagc                                           25

<210> SEQ ID NO 7
<211> LENGTH: 24
<212> TYPE: DNA
<213> ORGANISM: Artificial Sequence
<220> FEATURE:
<223> OTHER INFORMATION: Primer MA12aR

<400> SEQUENCE: 7
agggtcagtg gggccgaggg ccca                                            24

<210> SEQ ID NO 8
<211> LENGTH: 24
<212> TYPE: DNA
<213> ORGANISM: Artificial Sequence
<220> FEATURE:
<223> OTHER INFORMATION: Primer MA2SF

<400> SEQUENCE: 8
gattgggcga agccctccgg ctcg                                            24

<210> SEQ ID NO 9
<211> LENGTH: 24
<212> TYPE: DNA
<213> ORGANISM: Artificial Sequence
<220> FEATURE:
<223> OTHER INFORMATION: Primer MA1R

<400> SEQUENCE: 9
cccaaggggc aagaagcatg gcca                                            24

<210> SEQ ID NO 10
<211> LENGTH: 22
<212> TYPE: DNA
<213> ORGANISM: Artificial Sequence
<220> FEATURE:

<223> OTHER INFORMATION: Primer MA2SR

<400> SEQUENCE: 10
tcagtgcggc ccaggcccgc ag                                              22

<210> SEQ ID NO 11
<211> LENGTH: 58
<212> TYPE: DNA
<213> ORGANISM: Artificial Sequence
<220> FEATURE:
<223> OTHER INFORMATION: DNA segment described by FIG. 5

<400> SEQUENCE: 11
tgacttgggc ttagccagca cccaccaccc cacgcgccac cccacaaccc cgggtaga      58

<210> SEQ ID NO 12
<211> LENGTH: 1874
<212> TYPE: DNA
<213> ORGANISM: Homo sapiens
<220> FEATURE:
<221> NAME/KEY: misc_feature
<222> LOCATION: (1)..(1874)
<223> OTHER INFORMATION: HBA2 sequence (1874 bp) from FIG. 6

<400> SEQUENCE: 12
tctcccctgt cctttcccta cccagagcca agtttgttta tctgtttaca accagtattt      60
acctagcaag tcttccatca gatagcattt ggagagctgg gggtgtcaca gtgaaccacg     120
acctctaggc cagtgggaga gtcagtcaca caaactgtga gtccatgact tggggcttag     180
ccagcaccca ccaccccacg cgccacccca caaccccggg tagaggagtc tgaatctgga     240
gccgccccca gcccagcccc gtgcttttttg cgtcctggtg tttgttcctt cccggtgcct     300
gtcactcaag cacactagtg actatcgcca gagggaaagg gagctgcagg aagcgaggct     360
ggagagcagg aggggctctg cgcagaaatt cttttgagtt cctatgggcc agggcgtccg     420
ggtgcgcgca ttcctctccg ccccaggatt gggcgaagcc ctccggctcg cactcgctcg     480
cccgtgtgtt ccccgatccc gctggagtcg atgcgcgtcc agcgcgtgcc aggccggggc     540
gggggtgcgg gctgactttc tccctcgcta gggacgctcc ggcgcccgaa aggaaagggt     600
ggcgctgcgc tccggggtgc acgagccgac agcgcccgac cccaacgggc cggccccgcc     660
agcgccgcta ccgccctgcc cccgggcgag cgggatgggc gggagtggag tggcgggtgg     720
agggtggaga cgtcctggcc cccgccccgc gtgcacccccc aggggaggcc gagcccgccg     780
cccggccccg cgcaggcccc gcccgggact cccctgcggt ccaggccgcg ccccgggctc     840
cgcgccagcc aatgagcgcc gcccggccgg gcgtgccccc gcgccccaag cataaaccct     900
ggcgcgctcg cgggccggca ctcttctggt ccccacagac tcagagagaa cccaccatgg     960
tgctgtctcc tgccgacaag accaacgtca aggccgcctg gggtaaggtc ggcgcgcacg    1020
ctggcgagta tggtgcggag gccctggaga ggtgaggctc cctcccctgc tccgacccgg    1080
gctcctcgcc cgcccggacc cacaggccac cctcaaccgt cctggccccg gacccaaacc    1140
ccacccctca ctctgcttct ccccgcagga tgttcctgtc cttccccacc accaagacct    1200
acttcccgca cttcgacctg agccacggct ctgcccaggt aagggccac ggcaagaagg    1260 tggccgacgc gctgaccaac gccgtggcgc acgtggacga catgcccaac gcgctgtccg    1320
ccctgagcga cctgcacgcg cacaagcttc gggtggaccc ggtcaacttc aaggtgagcg    1380
gcgggccggg agcgatctgg gtcgaggggc gagatgcgc cttcctctca gggcagagga    1440
tcacgcgggt tgcgggaggt gtagcgcagg cggcggctgc gggcctgggc cgcactgacc    1500

| | |
|---|---|
| ctcttctctg cacagctcct aagccactgc ctgctggtga ccctggccgc ccacctcccc | 1560 |
| gccgagttca cccctgcggt gcacgcctcc ctggacaagt tcctggcttc tgtgagcacc | 1620 |
| gtgctgacct ccaaataccg ttaagctgga gcctcggtag ccgttcctcc tgcccgctgg | 1680 |
| gcctcccaac gggccctcct cccctccttg caccggccct tcctggtctt tgaataaagt | 1740 |
| ctgagtgggc agcagcctgt gtgtgcctgg gttctctcta tcccggaatg tgccaacaat | 1800 |
| ggaggtgttt acctgtctca gaccaaggac ctctctgcag ctgcatgggg ctggggaggg | 1860 |
| agaactgcag ggag | 1874 |

<210> SEQ ID NO 13
<211> LENGTH: 393
<212> TYPE: DNA
<213> ORGANISM: Homo sapiens
<220> FEATURE:
<221> NAME/KEY: misc_feature
<222> LOCATION: (1)..(396)
<223> OTHER INFORMATION: HBA12 sequence (396 bp) from FIG. 7

<400> SEQUENCE: 13

| | |
|---|---|
| gccctcggcc ccactgaccc tcttctctgc acagctccta agccactgcc tgctggtgac | 60 |
| cctggccgcc cacctccccg ccgagttcac ccctgcggtg cacgcctccc tggacaagtt | 120 |
| cctggcttct gtgagcaccg tgctgacctc caaataccgt taagctggag cctcggtagc | 180 |
| cgttcctcct gcccgctggg cctcccaacg ggccctcctc ccctccttgc accggccctt | 240 |
| cctggtcttt gaataaagtc tgagtgggca gcagcctgtg tgtgcctggg ttctctctat | 300 |
| cccggaatgt gccaacaatg gaggtgttta cctgtctcag accaaggacc tctctgcagc | 360 |
| tgcatggggc tggggaggga gaactgcagg gag | 393 |

<210> SEQ ID NO 14
<211> LENGTH: 1229
<212> TYPE: DNA
<213> ORGANISM: Homo sapiens
<220> FEATURE:
<221> NAME/KEY: misc_feature
<222> LOCATION: (1)..(1231)
<223> OTHER INFORMATION: HBA1 sequence (1231 bp) from FIG. 8

<400> SEQUENCE: 14

| | |
|---|---|
| tgtttattcc ttcccggtgc ctgtcactca agcacactag tgactatcgc cagagggaaa | 60 |
| gggagctgca ggaagcgagg ctggagagca ggaggggctc tgcgcagaaa ttcttttgag | 120 |
| ttcctatggg ccagggcgtc cgggtgcgcg cattcctctc cgcccaggga ttgggcgaag | 180 |
| cctcccggct cgcactcgct cgcccgtgtg ttccccgatc ccgctggagt cgatgcgcgt | 240 |
| ccagcgcgtg ccaggccggg cgggggtgc gggctgactt tctccctcgc tagggacgct | 300 |
| ccggcgcccg aaaggaaagg gtggcgctgc gctccgggt gcacgagccg acagcgcccg | 360 |
| accccaacgg gccggccccg ccagcgccgc taccgccctg cccccgggcg agcgggatgg | 420 |
| gcgggagtgg agtggcgggt ggagggtgga gacgtcctgg ccccgccccc gcgtgcaccc | 480 |
| ccaggggagg ccgagcccgc cgcccggcc cgcgcaggcc ccgcccggga ctcccctgcg | 540 |
| gtccaggccg cgccccgggc tccgcgccag ccaatgagcg ccgcccggcc gggcgtgccc | 600 |
| ccgcgcccca agcataaacc ctggcgcgct cgcggcccgg cactcttctg gtccccacag | 660 |
| actcagagag aacccaccat ggtgctgtct cctgccgaca agaccaacgt caaggccgcc | 720 |
| tgggggtaagg tcggcgcgca cgctggcgag tatggtgcgg aggccctgga gaggtgaggc | 780 |

```
tccctcccct gctccgaccc gggctcctcg cccgcccgga cccacaggcc accctcaacc       840
gtcctggccc cggacccaaa ccccacccct cactctgctt ctccccgcag gatgttcctg       900
tccttcccca ccaccaagac ctacttcccg cacttcgacc tgagccacgg ctctgcccag       960
gttaagggcc acggcaagaa ggtggccgac gcgctgacca acgccgtggc gcacgtggac      1020
gacatgccca acgcgctgtc cgccctgagc gacctgcacg cgcacaagct tcgggtggac      1080
ccggtcaact tcaaggtgag cggcgggccg ggagcgatct gggtcgaggg gcgagatggc      1140
gccttcctcg cagggcagag gatcacgcgg gttgcgggag gtgtagcgca ggcggcggct      1200
gcgggcctgg gccctcggcc ccactgacc                                       1229
```

SINGLE TUBE MULTIPLEX PCR METHOD FOR THE DETECTION OF HBA1, HBA2 AND HBA12 GENES

REFERENCE TO A SEQUENCE LISTING

In accordance with 37 CFR § 1.52(e)(5), the present specification makes reference to a Sequence Listing which is submitted herewith electronically as a .txt file named "481382us_ST25.txt". The .txt file was generated on Nov. 12, 2018 and is 3,090 bytes in size. The entire contents of the Sequence Listing are herein incorporated by reference.

BACKGROUND

Field of the Invention

The invention pertains to the fields of medicine, genetics, and immunology.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

HBA Genes. The HBA1 and HBA2 gene sequences encode alpha globin proteins. The HBA1 gene provides instructions for making a protein called alpha-globin and this protein is also produced from a nearly identical gene called HBA2. These two alpha-globin genes are located close together in a region of chromosome 16 known as the alpha-globin locus. They are homologous in nature and show frequent intergenic exchange; Michelson, A. M.; and Orkin, S. H.; (1983). *Boundaries of gene conversion within the duplicated human alpha-globin genes. Concerted evolution by segmental recombination.* Journal of Biological Chemistry. 258(24): pp. 15245-15254; Law, H. Y.; Luo, H. Y.; Wang, W.; Ho, J. F.; Najmabadi, H. Ng. IS.; Steinberg, M. H.; Chui D. H.; Chong, S. S. (2006), *Determining the cause of patchwork HBA1 and HBA2 genes: recurrent gene conversion or crossing over fixation events.* Haematologica. 91(3):297-302; Hardison, R. C., (2012). *Evolution of hemoglobin and its genes.* Cold Spring Harbor perspectives in medicine. 2(12): p. a011627; Borgio et al., id. 2014; Borgio, id. 2015).

HBA1 and HBA2 as well as their mutant forms have a high degree of molecular similarity and gene conversion between HBA and HBA2 in the alpha globin locus region is well documented and recently it has been discovered that the HBA2 has been replaced by a unique HBA12 gene conversion in 5.7% of the Saudi population. Direct sequencing of the HBA2 and HBA1 genes from 157 Saudi subjects revealed a new HBA2 gene conversion in cis or trans in 5.7% of these subjects. This new HBA2 gene convert is referred to as the α12 (HBA12) allele due to its combination of α1 (HBA1) and α2 (HBA2) sequences; see Borgio, J. F.; AbdulAzeez, S., Al-Nafie, A. N., Naserullah, Z. A., Al-Jarrash, S., *A novel HBA2 gene conversion in cis or trans: "alpha12 allele" in a Saudi population*, Blood Cells, Molecules and Diseases. 53: 199-203 (2014) and Borgio, J. F., *Molecular nature of alpha-globin genes in the Saudi population*, Saudi Medical Journal 36:1271-1276 (2015).

HBA12 Gene. The HBA12 gene allele comprises parts of the HBA1 gene (promoter, intron 1, coding region 2, intron 2) in its upstream region, while downstream of HBA12 gene is indistinguishable from the HBA2 gene (part of intron 2 and exon 3); Borgio et al., id. 2014, id.; Borgio, id. 2015. The HBA12 gene has the region starting −6 bp until 581 bp (3' promoter, exon1, IVSI, exon2, and 5'IVSII) from HBA1 gene, and 774 bp (3'enhancer) onwards from HBA2 gene; and a total of 5.7% of the study population including sickle cell trait, hemophilia-A patient, SCD patients, and β-thal major patients were reported to have the new gene convert, $α_{12}$ gene; Borgio, id. (2014).

Reduced HBA2 in HBA12 patients. A reduced level of HBA2 was observed in the first five (HbS$^{carrier}$; β-thal$^{carrier}$; β-thal$^{major}$/α-thal$^{carrier}$; SCD$^{+ve}$, and α-thal$^{carrier}$; HbS$^{carrier}$ α-thal$^{carrier}$) of six different subgroups of Saudis who carried HBA12; Borgio, et al., id. (2014). These groups as well as 32 different genotypes reported in the Saudi population are incorporated by reference to Borgio, et al., id. (2014). The presence of HBA12 genotypes α1α12/α1α12, α1-/α1α12, α1α2/α1α12, −α23.7/α1α12, and α1-4.2/α1α12 is associated with a reduced level of HBA2 (α262) in β-thalassemia carriers, which might give a false negative result in conventional tests; Borgio et al., id., 2014.

The HBA12 gene conversion presents challenges to conventional tests that only measure HBA1 or HBA2 and there is a need for a simple test that can be used for large scale screening of populations, like the Saudi population, where HBA12 is prevalent in order to proper asses the disease burden in these populations; Borgio, et al., id. (2015); Akhtar, M. S., Qaw, F., Borgio, J. F, Albuali, W., Suliman, A., Nasserullah, Z., Al-Jarrash, S. and Al-Ali, A., *Spectrum of α-thalassemia mutations in transfusion dependent β-thalassemia patients from the Eastern Province of Saudi Arabia.* Hemoglobin. 37(1): 65-73 (2013).

Alpha-thalassemia (α-thal) is a disorder caused by the deletion of single or double α-globin genes, and/or point mutations in the α-globin genes. The α-globin genes, such as HBA1 and HBA2 have been emerging as a molecular target for the treatment of β-thalassemia (β-thal), for example, reduced synthesis of α-globin protein can ameliorate the clinical severity of β-thalassemia. Hence, it is essential to understand the molecular nature of α-globin genes to treat the most prevalent hemoglobin disorders, such as sickle cell disease, α-thal, and β-thal prevalent in the Kingdom of Saudi Arabia. Many alpha globin genotypes from the Eastern Region of Saudi Arabia, such as α1α12/α1α12, α1-/α1α12, α1α2/α1α12, α23.7/α1α12, and α1-4.2/α1α12 have been identified, see Borgio et al., id., 2014 and these genotypes have been observed in subjects having sickle cell disease (SCD), sickle cell trait, β-thalassemia major and in β-thal carriers; Borgio et al., id., 2014. These and other genotypes associated with these diseases are incorporated by reference to Borgio, et al., id. 2014) and Borgio, et al. id. 2015. The HBA12 genotypes α1α12/α1α12, α1-/α1α12, α1α2/α1α12, −α123.7/2, and α1-4.2/α1α12 have been associated with the level of HBA2 and a high level of HBA2 is considered to be a marker for the presence of the β-thalassemia mutation.

In view of the limitations of conventional techniques, especially with regard to Saudi patients having an HBA12 genotype, the inventors sought to develop a multiplex PCR-based method that accurately identifies HBA12 genotypes along with related alpha globin genotypes, such as the HBA1 and HBA2 genotypes, as well as a test that avoids false positive frameshift mutations due to deletion of a region containing 5' CTCGGCCC 3' with an objective of diagnosing genetic diseases and disorders such as thalassemia and sickle cell anemia as well as the associated carrier states.

BRIEF SUMMARY OF THE INVENTION

In one embodiment, the invention is directed to a multiplex polymerase chain reaction (PCR) based method that simultaneously detects the HBA1, HBA2 and HBA12 genes in a biological sample. This method is particularly useful in geographic regions like Saudi Arabia where a significant percentage of the population carry the HBA12 gene conversion or convert. This method simultaneously targets three different alpha globin genes HBA1, HBA2 and HBA12 in a biological a sample quickly, with high sensitivity, and at low cost. This avoids situations where conventional PCR primers for the HBA1 and HBA2 genes cannot amplify the HBA12 gene because the HBA12 gene results from patchwork between the HBA1 and HBA2 genes. Only a single PCR procedure is required to provide diagnosis based on detection of these three genes thus minimizing the cost and time of conducing separate tests and the HBA1, HBA2, HBA12 multiplex PCR described herein was engineered in such a way as to detect all the possible combinations as described in FIG. 1D and FIG. 4. The method may be used in hospitals, diagnostic laboratories, forensic laboratories, and research laboratories.

Additional, non-limiting embodiments of this technology include the methods and products described below.

One embodiment of the invention is method for determining an HBA genotype and/or treating a subject at risk of a hemoglobin A (HBA) associated disease or trait comprising detecting Hemoglobin alpha 1 (HBA1) gene, Hemoglobin alpha 2 (HBA2) gene, and Hemoglobin alpha 12 (HBA12) genes in the subject, including: obtaining a sample from the subject; contacting the sample with at least one set of primers for each of HBA1, HBA2 and HBA12 under conditions suitable for the primers to amplify DNA in the sample by multiplex polymerase chain reaction (PCR), wherein the set of HBA1 primers are MA1F (SEQ ID NO: 3) and MA12R (SEQ ID NO: 4), the set of HBA2 primers are MA2F (SEQ ID NO: 5) and MA2R (SEQ ID NO: 2 or 6) and the set of HBA12 primers are MA12F (SEQ ID NO: 1) and MA2R (SEQ ID NO: 2 or 6), detecting presence of, or levels of, HBA1, HBA2 and HBA12 DNA amplified by each primer, thereby detecting a genotype of the subject, and, for a method of treatment, treating the subject for an HBA associated disease or trait when a genotype associated with an HBA disease or trait is detected. In some embodiments, the subject carries gene conversion HBA12 and in other embodiments subject does not carry gene conversion HBA12.

The method described in the embodiments above may be performed using a biological sample that is blood, plasma or serum, or white blood cells, or cells obtained from a buccal swab. In some embodiments a biological sample may be obtained from storage, such as from a bank of cell samples or DNA.

The primers for HBA1, HBA2 and HBA12 may be part of a single primer pool.

The embodiments described above may further include selecting a subject at risk of sickle cell disease when the presence of amplified HBA1, HBA2 and/or HBA12 is detected; and/or may further include selecting or characterizing or treating a subject having sickle cell trait or sickle cell disease when the presence of amplified HBA1, HBA2 and/or HBA12 is detected. In other related embodiments the method may further include selecting a subject at risk of sickle cell disease when the presence of amplified HBA1, HBA2 and/or HBA12 is detected and treating the subject for sickle cell disease with at least one of penicillin, hydroxyurea, a transfusion of red blood cells transfusion, by hematopoietic stem cell transplantation, by gene therapy of by other modes of treatment described herein.

In some embodiments a method disclosed herein includes selecting a subject at risk of thalassemia when the presence of amplified HBA1, HBA2 and/or HBA12 is detected; and/or it may also include selecting a subject at risk of thalassemia when the presence of amplified HBA1, HBA2 and HBA12 is detected and treating the subject for thalassemia with at least one of a blood transfusion, iron chelation therapy, folic acid, or the other treatment modes described herein.

Another embodiment of the invention involves a primer pool composition comprising a set of primers for each of HBA1, HBA2 and HBA12, wherein the set of HBA1 primers are MA1F (SEQ ID NO: 3) and MA12R (SEQ ID NO: 4), the set of HBA2 primers are MA2F (SEQ ID NO: 5) and MA2R (SEQ ID NO: 2 or 6) and the set of HBA12 primers are MA12F (SEQ ID NO: 1) and MA2R (SEQ ID NO: 2 or 6). A related embodiment involves a composition including one or more human DNA samples or templates and the primer pool of embodiment 12, and optionally positive or negative control samples from subjects not having a thalassemia or sickle cell disease or trait. Such a composition can also include human nucleic acid sample or template, the primer pool of embodiment 11, a DNA polymerase, dNTPs, a buffer solution, and bivalent cations, monovalent cations.

Another embodiment of the invention is a pair or pairs of primers that amplify at least one of HBA1, HBA2 and/or HBA12, selected from the group consisting of HBA1 primers MA1F (SEQ ID NO: 3) and MA12R (SEQ ID NO: 4); HBA2 primers MA2F (SEQ ID NO: 5) and MA2R (SEQ ID NO: 2 or 6); and HBA12 primers MA12F (SEQ ID NO: 1) and MA2R (SEQ ID NO: 2 or 6). Amplification is preferably performed in a single PCR tube will a combination of these primers, but in some embodiments may be performed sequentially or in parallel with individual primer pairs.

Related embodiments include a composition that includes HBA1 primers MA1F (SEQ ID NO: 3) and MA12R (SEQ ID NO: 4); HBA2 primers MA2F (SEQ ID NO: 5) and MA2R (SEQ ID NO: 2 or 6); and/or HBA12 primers MA12F (SEQ ID NO: 1) and MA2R (SEQ ID NO: 2 or 6).

In some embodiments, the method described above may be practiced with a chemically-modified primer selected from the group consisting of MA1F (SEQ ID NO: 3) and MA12R (SEQ ID NO: 4), MA2F (SEQ ID NO: 5) and MA2R (SEQ ID NO: 2 or 6), MA12F (SEQ ID NO: 1), MA12aR (SEQ ID NO: 7), MA2SF (SEQ ID NO: 8), MA1R (SEQ ID NO: 9) or MA2SR (SEQ ID NO: 10); wherein said primer has been modified (a) by conjugation to a fluorescent tag, biotin, quencher or other detectable reporter moiety and/or by substitution of a chemically modified, non-natural nucleotide for at least one dA, dC, dG or dT in MA1F (SEQ ID NO: 3) and MA12R (SEQ ID NO: 4), MA2F (SEQ ID NO: 5) and MA2R (SEQ ID NO: 2 or 6), MA12F (SEQ ID NO: 1), MA12aR (SEQ ID NO: 7), MA2SF (SEQ ID NO: 8), MA1R (SEQ ID NO: 9) or MA2SR (SEQ ID NO: 10). Other embodiments include compositions and individual primer pairs including the chemically-modified forms of the primers described herein.

Another embodiment is directed to premarital test or other genetic test kit comprising a set of primers for each of HBA1, HBA2 and HBA12, wherein the set of HBA1 primers are MA1F (SEQ ID NO: 3) and MA12R (SEQ ID NO: 4), the set of HBA2 primers are MA2F (SEQ ID NO: 5) and MA2R (SEQ ID NO: 2 or 6) and the set of HBA12 primers are MA12F (SEQ ID NO: 1) and MA2R (SEQ ID NO: 2 or 6), and, optionally, buccal swab(s), sample containers optionally containing preservatives for DNA, packaging materials, return mail or courier envelopes or containers, and instructions for use for assessing a risk of sickle cell anemia, sickle cell trait, or thalassemia or thalassemia trait.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1D describes a model multiplex PCR for the identification of $\alpha$12 and its genotypes. The amplicons for FIGS. 1A, 1B and 1C are respectively shown by FIGS. 6, 7 and 8 and by SEQ ID NOS: 12, 13 and 14. As shown in FIG. 1D, lane 1, the normal $\alpha$1$\alpha$2/$\alpha$1$\alpha$2 genotype shows the $\alpha$1 and $\alpha$2 amplicons, but not the $\alpha$12 amplicon. Lanes 2-7 show patterns characteristics of the other genotypes depicted at the top of the figure.

FIG. 2. Manually designed primers for amplification of HBA1, HBA2 and HBA12 genes.

FIG. 3A. Multiplex PCR results. Lane L: 100 bp Ladder; Lanes 1 to 11: Multiplex PCR result for various samples; and Lane AL: Allelic ladder. An 1874 bp amplicon ($\alpha$2) is visible in lands 5, 6, 8-10 and AL. A 1231 bp amplicon ($\alpha$1) appears in lanes 1-11 and AL and a 396 bp amplicon ($\alpha$2) appears in lanes 2, 11 and AL.

FIG. 3B. Multiplex PCR results. Lane L: 100 bp Ladder; Lane AL: Allelic ladder showing the positions of each amplicon, respectively from top: $\alpha$2 (1874 bp), $\alpha$1 (1231 bp) and $\alpha$12 396 bp). Sample 1 and the Allelic ladder show the band corresponding to the $\alpha$12 amplicon.

FIG. 3C. Multiplex PCR results-location of non-specific bands. Lanes X, Y and Z: Highlighted green color bands (between the upper band and the two lower bands) denote the non-specific PCR products. Lane AL: Allelic ladder.

FIG. 6. Nucleotide sequence of the PCR product from the primer pair MA2F and MA2R from the HBA12 gene with the sequence length of 1874 bp long. This sequence appears as SEQ ID NO: 12.

FIG. 7. Nucleotide sequence of the PCR product from the primer pair MA12F and MA2R from the HBA12 gene with the sequence length of 396 bp long. This sequence appears as SEQ ID NO: 13.

FIG. 8. Nucleotide sequence of the PCR product from the primer pair MA1F and MA12R from the HBA1 gene with the sequence length of 1231 bp long. This sequence appears as SEQ ID NO: 14.

DETAILED DESCRIPTION OF THE INVENTION

Figures 1A, 1B, 1C, 1D:
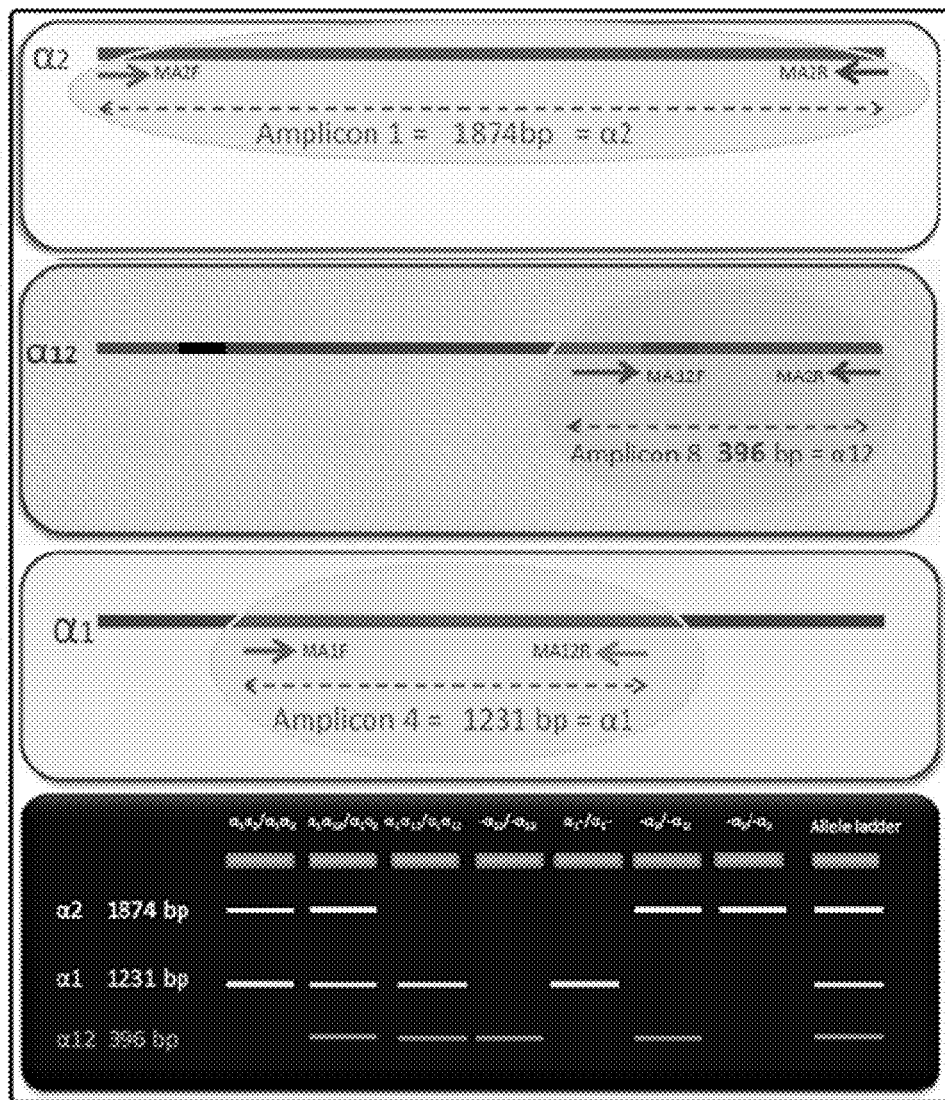
FIGS. 1A-1D. Primer sites and amplicon size for the multiplex amplification of the HBA1 ($\alpha$1), HBA2 ($\alpha$2) and HBA12 ($\alpha$2) genes, see FIGS. 1A, 1B and 1C, respectively.

The multiplex PCR method disclosed herein may be used to identify or characterize the HBA genotype of a person, such as a patient or a subject at statistical risk of carrying an HBA12 gene conversion. A patient or subject to be diagnosed, treated, or diagnosed and treated with a method disclosed herein may be a normal subject having a genotype not associated with disease, a carrier or a subject carrying a disease trait, such as sickle cell trait, or a patient having a disease or disorder associated with HBA1, HBA2 and/or HBA12. Genotypes such as those described by FIG. 4 may be easily and inexpensively determined by the multiple PCR method of the invention.

Hemoglobin genes. For practical purposes, the two alpha globin genes (termed alpha1 and alpha2) are identical. The HBA2 ($\alpha_2$) and HBA1 ($\alpha_1$) coding sequences are identical. These genes differ slightly over the 5' untranslated regions and the introns, but they differ significantly over the 3' untranslated regions. Since each normal cell has two chromosomes 16, a total of four alpha globin genes exist in each cell. Each of the four genes produces about one-quarter of the alpha globin chains needed for hemoglobin synthesis.

Hemoglobin A1 also known as Hemoglobin A (HbA), adult hemoglobin, or $\alpha_2\beta_2$, is the most common human hemoglobin tetramer, comprising over 97% of the total red blood cell hemoglobin. It consists of two alpha chains and two beta chains; see *Hemoglobinopathies*, revised Apr. 17, 2002, hypertext transfer protocol://sickle.bwh.harvard.edu/hemoglobinopathy.html (last accessed Oct. 30, 2018, incorporated by reference).

Hemoglobin A2 is a normal variant of hemoglobin A that consists of two alpha and two delta chains ($\alpha_2\delta_2$) and is found at low levels in normal human blood. Hemoglobin A2 may be increased in beta thalassemia or in people who are heterozygous for the beta thalassemia gene. HBA2 exists in small amounts in all adult humans (1.5-3.1% of all hemoglobin molecules) and is approximately normal in people with sickle-cell disease; *Hemoglobinopathies*, id. (2002).

Hemoglobin A12. The HBA12 gene comprises parts of the HBA1 gene (promoter, intron 1, coding region 2, intron 2) in its upstream region, while downstream of HBA12 gene is indistinguishable from the HBA2 gene (part of intron 2 and exon 3) (Borgio et al., id. 2014, id.; Borgio, id. 2015). The intergenic exchange between the HBA1 and HBA2 genes was observed among 5.7% of Saudis (Borgio et al., id. 2014; Borgio, id. 2015).

Thalassemia. The thalassemias are a group of disorders in which the normal hemoglobin protein is produced in lower amounts than usual. The genes are defective in the amount of hemoglobin they produce, but that which they produce (generally) is normal. The thalassemias are a complex group of disorders because of the genetics of hemoglobin production and the structure of the hemoglobin molecule.

There are four kinds of alpha thalassemia: (i) Alpha thalassemia silent carrier. One gene is missing or damaged, and the other 3 are normal. Blood tests are usually normal.

A patient's red blood cells may be smaller than normal. Being a silent carrier means there are no signs of the disease, but one can pass the damaged gene on to one's offspring. This is confirmed by DNA tests. (ii) Alpha thalassemia carrier. Two genes are missing. A subject may have mild anemia. (iii) Hemoglobin H disease. Three genes are missing. This leaves just 1 working gene. A patient may have moderate to severe anemia and symptoms can worsen with fever or get worse when a patient is exposed to certain medicines, chemicals, or infectious agents. Blood transfusions are often needed. Such a patient generally has a greater risk of having a child with alpha thalassemia major. (iv) Alpha thalassemia major occurs when four HBA genes are missing. This causes severe anemia and in most cases a baby with this condition will die before birth.

Both alpha- and beta-forms of thalassemia major can cause significant complications. For example, people with thalassemia can get too much iron in their bodies, either from the disease itself or from frequent blood transfusions. The iron overload can result in damage to the heart, liver and endocrine system which includes glands that produce hormones that regulate processes throughout the body. Bone deformities are also common since thalassemia can make the bone expand, causing bone to widen. Thalassemia is also often accompanied by the destruction of a large number of red blood cells, making the spleen to work harder than normal and enlarge (splenomegaly). Splenomegaly can make anemia worse and reduce the life of transfused red blood cells. If the spleen grows too big, it will have to be surgically removed. People with thalassemia major have an increased risk of infection. This is especially true when the spleen has been removed from the patient's body due to the aforementioned severe splenomegaly.

Infections are major complications for thalassemia patients and constitute the second most common cause of mortality and morbidity for these patients. Major causative organisms of bacterial infections in thalassemic patients include *Klebsiella* sp., *Candida albicans, Staphylococcus aureus, Yersinia enterocolitica, Pseudomonas* sp. and *Streptococcus pneumoniae*. For most of these bacteria, vaccines are not available. Where infection is suspected, the main causes to be considered include splenectomy, transmission of pathogens by blood transfusions, iron overload and iron chelation. As the body's immune system of a thalassemic patient is already sharply suppressed due to a reduction in neutrophil numbers, it is crucial to reduce mortality by recognizing and presumptively treating infections in a patient as quickly as possible. PCR-based methods facilitate the detection of pathogenic DNA components in biological samples, see Vosberg, Human Genetics 83(1):1-15, 198 which is incorporated reference). Treatment of a subject identified or characterize as having, or at risk of having, thalassemia may include treatment of an infection with an antibiotic or other anti-microbial agent that kills or inhibits the growth of the microorganisms described above or other infectious microbes in the subject.

Treatment of alpha thalassemia may include: daily doses of folic acid; blood transfusions (as needed); surgery to remove the spleen; medicines to reduce extra iron in the body (iron chelation therapy) such as Deferoxamine or Deferasirox); avoidance of oxidant drugs in hemoglobin H disease; transplantation of blood or bone marrow stem cells from a healthy donor or with genetically modified homologous cells (gene therapy) correcting the defect in HBA levels. Genetic counseling may also be used as a preventative treatment to reduce the risk of offspring having or carrying alpha thalassemia or sickle cell disease. Typically, thalassemia major patients are treated by regular blood transfusions and chelation therapy. Individuals positive for the HBA12 gene (see FIGS. 4B, 4C, 4F and 4H) and borderline HbA$_2$ are considered as beta thalassemia carriers.

Sickle Cell Disease and Trait. Normally, humans have hemoglobin A, which consists of two alpha and two beta chains, hemoglobin A2, which consists of two alpha and two delta chains, and hemoglobin F, consisting of two alpha and two gamma chains in their bodies. Out of these three types, hemoglobin F dominates until about 6 weeks of age. Afterwards, hemoglobin A dominates throughout life. In people diagnosed with sickle cell disease, at least one of the β-globin subunits in hemoglobin A is replaced with what's known as hemoglobin S. In sickle cell anemia, a common form of sickle cell disease, hemoglobin S replaces both β-globin subunits in the hemoglobin.

Sickle cell conditions have an autosomal recessive pattern of inheritance from parents. The types of hemoglobin a person makes in the red blood cells depend on what hemoglobin genes are inherited from her or his parents. If one parent has sickle cell anemia and the other has sickle cell trait, then the child has a 50% chance of having sickle cell disease and a 50% chance of having sickle cell trait. When both parents have sickle cell trait, a child has a 25% chance of sickle cell disease, 25% do not carry any sickle cell alleles, and 50% have the heterozygous condition.

Treatment of sickle cell disease and trait include any of the treatments described by the Centers for Disease Control (CDC) at hypertext transfer protocol secure://worldwide web.cdc.gov/ncbddd/sicklecell/treatments.html (incorporated by reference). Drug treatments include hydroxyurea, antibiotics, folic acid, vitamin E and NSAIDS, opioids and other analgesics.

Blood transfusions may be used to treat symptoms of SCD. Many Saudi SCD patients are presently treated with hydroxyurea to reduce pain and by therapeutic transfusions of red blood cells. In addition, transplantation of blood or bone marrow stem cells from a healthy donor or transfer of genetically modified homologous cells (gene therapy) that produce normal, non-Sickle cells. Genetic counseling may also be used as a preventative treatment to reduce the risk of offspring having or sickle cell disease.

Biological sample. A biological sample is a sample that contains a nucleic acid detectable by PCR. A sample may contain genomic DNA as well as RNA. Representative biological samples include whole blood, plasma, serum, buffy coat cells, and cells from a buccal swab. Other samples may include spinal fluid, synovial fluid, lymph fluid, saliva, sputum, mucosal secretions, urine, and other biological fluid, cells, or tissues. In some embodiments a sample may contain cells obtained from an individual that have been cultured in vitro or which have been frozen or otherwise preserved. In some embodiments, a biological sample will contain a preservative, such as EDTA or a buffer or be isolated from other components in an original biological sample, such as proteins. The nucleic acid may be isolated from a cell or be isolated from a non-cellular material, such as cell-free DNA (cfDNA) from blood plasma or serum. Preferably, a sample will be obtained non-invasively.

Samples may be obtained from normal subjects, subjects deemed at risk of developing an HBA associated disease, disorder or condition, or subjects already diagnosed with such a disease, disorder or condition. Samples may be taken from subjects for routine screening, from family members of a patient, such as from a grandparent, parent, sibling or cousin, from a person prior to marriage or prior to a pregnancy, from a pregnant woman or from a subject in utero.

Polymerase Chain Reaction (PCR). The present invention relates to primers as well as primer pools comprising multiple primer pairs or a primer pool that recognize, anneal to and simultaneously amplify targeted HBA1, HBA2 and HBA12 genes. The practice of the present invention will employ, unless otherwise indicated, conventional techniques of molecular biology, microbiology and recombinant DNA techniques, which are within the skill of the art including various multiplex PCR procedures including quantitative PCR. Such techniques are explained fully in the literature and specific recipes and conditions for PCR reactions are provided in the examples; see, e.g., Sambrook, Fritsch & Maniatis, *Molecular Cloning; A Laboratory Manual*, Second Edition, (1989) (hereinafter "Maniatis"); *Oligonucleotide Synthesis* (M. J. Gait, ed., 1984); Nucleic Acid Hybridization (B. D. Hames & S. J. Higgins, eds., 1984); *A Practical Guide to Molecular Cloning* (B. Perbal, 1984); and a series, Methods in Enzymology (Academic Press, Inc.)—each incorporated herein by reference in its entirety.

Other multiplex PCR methods are described and incorporated by reference to: hypertext transfer protocol secure:// en.wikipedia.org/wiki/Multiplex_polymerase_chain_reaction (last accessed Nov. 12, 2018); Abbs, S; Bobrow, M (1992). "*Analysis of quantitative PCR for the diagnosis of deletion and duplication carriers in the dystrophin gene*". *Journal of Medical Genetics*. 29 (3): 191-96; Morlan, John; Baker, Joffre; Sinicropi, Dominick (2009). "*Mutation Detection by Real-Time PCR: A Simple, Robust and Highly Selective Method*". *PLoS ONE*. 4 (2): e4584; hypertext transfer protocol secure://worldwide web.sciencedirect.com/topics/agricultural-and-biological-sciences/multiplex-polymerase-chain-reaction (last accessed Nov. 11, 2018); and Elnfro, et al., Clin Microbiol Rev. 2000 October; 13(4): 559-570; hypertext transfer protocol secure://worldwide web.ncbi.nlm.nih.gov/pmc/articles/PMC88949/(last accessed Nov. 11, 2018).

As used herein, the terms "polynucleotide" and "oligonucleotide" refer to primers, probes, oligomer fragments to be detected, oligomer controls and unlabeled blocking oligomers and shall be generic to polydeoxy-ribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "polynucleotide" and "oligonucleotide", and these terms will be used interchangeably. These terms refer only to the primary structure of the molecule. Thus, these terms include double- and single-stranded DNA, as well as double- and single-stranded RNA.

The term "primer" may refer to more than one primer and refers to a single-stranded oligonucleotide, whether occurring naturally, as in a purified restriction digest, or produced synthetically, which is capable of acting as a point of initiation of synthesis along a complementary strand when placed under conditions in which synthesis of a primer extension product or amplicon, as used herein, which is complementary to a nucleic acid strand is catalyzed.

Such conditions include the presence of four different deoxyribonucleoside triphosphates and a polymerization-inducing agent such as a thermostable nucleotide polymerase, DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

As used herein, the term "target sequence" refers to a region of the polynucleotide which is to be amplified and/or detected, such as sequences forming all or part of an HBA1, HBA2 or HBA12 gene. "Target gene" refers to a target sequence wherein the region of the polynucleotide is a full functional gene of an organism that codes for a polypeptide or for an RNA chain that has a function in the organism.

As used herein, the term "thermostable nucleotide polymerase" refers to an enzyme which is relatively stable to heat when compared to nucleotide polymerases from *E. coli* and which catalyzes the polymerization of nucleosides. Generally, the enzyme will initiate synthesis at the 3-end of the target sequence utilizing the primer, and will proceed in the 3-direction along the template until synthesis terminates. A representative thermostable enzyme isolated from *Thermus aquaticus* (Taq) is described in U.S. Pat. No. 4,889,818 and a method for using it is described in Saiki et al., (1988), Science 239:487 (both incorporated herein by reference in their entirety). In one advantageous embodiment the multiplex PCR was performed by testing and selecting an annealing temperature ranging from 65, 66, 67, 78, 69, to 70° C.; testing and selecting an annealing time ranging from 1, 1.25, 1.5, 1.75 to 2 minutes. The quantity of primers was selected to range between 0.5, 1, 1.5, 2, 2.5 to 3 µl per primer at a primer concentration of 10 µM and the number of cycles were selected so as to provide for the proper appearance of the amplicons. The reaction volume ranging from 25, 30, 35, 40, 45 to 50 µl was selected.

In some embodiments, the primers disclosed herein may be used in a quantitative PCR method, such as a method that employs TaqMan hydrolysis probes. Such methods are known and incorporated by reference to hypertext transfer protocol secure://en.wikipedia.org/wiki/TaqMan (last accessed Nov. 13, 2018) and hypertext transfer protocol secure://en.wikipedia.org/wiki/Real-time_polymerase-_chain_reaction (last accessed Nov. 13, 2018).

Primers developed by the inventors. The following ten primers may be used in the multiplex PCR based method of the invention, preferably, primers having SEQ ID NOS: 1-6 are used based on their high specificity and sensitivity for amplifying DNA encoding HBA12.

| SEQ ID NO: | Name of the primer | Sequence (5'->3') |
|---|---|---|
| 1 | MA12F | GCCCTCGGCCCCACTGACCCTCTT |
| 2 | MA2R | CTCCCTGCAGTTCTCCCTCCCCAGC |
| 3 | MA1F | TGTTTATTCCTTCCCGGTGCCTGTCACTCAA |
| 4 | MA12R | AGGGTCAGTGGGGCCGAGGGCCCAGG |
| 5 | MA2F | TCTCCCCTGTCCTTTCCCTACCCAGAGC |
| 6 | MA2R | CTCCCTGCAGTTCTCCCTCCCCAGC |
| 7 | MA12aR | AGGGTCAGTGGGGCCGAGGGCCCA |
| 8 | MA2SF | GATTGGGCGAAGCCCTCCGGCTCG |
| 9 | MA1R | CCCAAGGGGCAAGAAGCATGGCCA |
| 10 | MA2SR | TCAGTGCGGCCCAGGCCCGCAG |

In some embodiments primers that amplify other genes associated with BA-related status may be included, for example, primers that amplify the ARTX gene.

Modified primers. In some embodiments of the invention, PCR or other primer-based nucleic acid detection techniques may be performed with a modified primer, such as a primer of SEQ ID NO: 1-10 that is labeled with a reporter fluorophone and/or a quencher molecule. Such reporters and quenchers are known in the art, see, for example, hypertext transfer protocol secure://worldwide web.bio-rad.com/en-us/applications-technologies/introduction-pcr-primer-probe-chemistries?ID=LUSOJW3Q3 (incorporated by reference, last accessed Oct. 30, 2018).

Primer modifications include, but are not limited to, substitution in an oligonucleotide of: 2-aminopurine for dA; 2,6-diaminopurine for dA; deoxyuridine (dU) for dT; 5-methyl dC for dC to increase Tm up to 0.5° C.; hydroxymethyl dC for dC; or deoxyinosine or 5-nitroindole as a "universal base" for any dA, dC, dG or dT in an oligonucleotide primer. Additional modifications include the incorporation or substitution of 5-hydroxybutynl-2'-deoxyuridine which is a duplex stabilizing modified base; incorporation or substitution of 8-aza-7-deazaguanosine that eliminates naturally occurring, non-Watson-and-Crick secondary structures associated with guanine-rich sequences; substitution of a locked nucleic acid base which has a modification to its ribose backbone that locks the base into a C3'-endo position, for one or more nucleotides in a primer. Other modifications include incorporation of inverted dT at a 3'-end of an oligonucleotide to inhibit degradation by 3' exonucleases or extension by DNA polymerases; incorporation of inverted dideoxy-T at a 5' end of a sequence to prevent unwanted 5' ligations, or incorporation of dideoxy-C as a 3' chain terminator. Other modifications are incorporated by reference to hypertext transfer protocol secure://worldwide web.idtdna.com/site/Catalog/Modifications/Category/7 (last accessed Nov. 7, 2018) or the 3', internal, or 5' modifications described by and incorporated by reference to hypertext transfer protocol secure://worldwide web.thermofisher.com/us/en/home/life-science/oligonucleotides-primers-probes-genes/custom-dna-oligos/oligo-configuration-options.html#5prime (last accessed Nov. 7, 2018). One, two, three or more of these modifications may be incorporated into an oligonucleotide primer sequence, such as those of SEQ ID NOS: 1-9, disclosed herein. A primer may also be modified by addition of a modified base, such as those described above at a 5' or 3' end. Advantageously, the method of the invention may be performed efficiently, simply and at low cost using unmodified primers.

Kits. Another aspect of the invention is a kit for determining HBA genotype using the multiplex PCR methods described herein. Such a kit may include one or more of a buccal swab, a blood collection device or other device for taking a biological sample, a PCR tube containing the primers disclosed herein, such as primers having SEQ ID NOS: 1-10, dNTPs, a DNA polymerase, control templates, molecular weight standards such as ladders or allelic ladders, as well as equipment for performing a PCR. In other embodiments, the kit may contain the primers disclosed herein and reagents for quantitative PCR. Such kits may also contain packaging materials, envelopes or containers for shipping biological samples, instructions for use and for communicating the test results, such as a web address or postal or shipping envelope.

Correlations with disease. The table below correlates particular patient status with HBA genotypes, for example, a normal subject may carry two copies of α1 and two copies of α12. Other disease or trait correlations may be determined using the chart below. The multiplex PCR method of the invention may be used to determine a person's genotype and thus provide useful information about their status. Other correlations between α1, α2 and α12 genotype and patient status are disclosed by and incorporated by reference to Borgio, Saudi Med J. 2015 November; 36(11): 1271-1276, see, for example, Table 1 and FIG. 2 of that reference.

| Condition | HBA Genotypes |
| --- | --- |
| Normal | a12/a1 |
| | a12/a1 |
| Silent α-thal | a12/— |
| | a12/a1 |
| Heterozygous | —/— |
| α-thal trait | a12/a1 |
| Homozygous | a12/— |
| α-thal trait | a12/— |
| HbH disease | a12/— |
| | —/— |
| Hb Bart's | —/— |
| | —/— |
| Sickle Cell | |
| Sickle Cell trait | |

Correlations Between Multiplexing PCR Results and Sickle Cell Anemia and Thalassemia.

Identification or characterization of a patient as having an a12/a1, a12/a1 genotype and as being in normal condition may trigger a decision to provide genetic counselling classifying the subject as one with little or no risk of having a child with alpha-thalassemia, to remove the patient from a treatment for thalassemia, or to substitute a different treatment not based on misdiagnosis of thalassemia or SCD. Identification or characterization of a patient as having an a12/--, a12/a1 genotype and as having silent alpha thalassemia may trigger a decision to provide genetic counseling, such as premarital counseling, to explain the risks of a child having alpha thalassemia; or to remove the patient from a treatment for thalassemia.

Identification or characterization of a patient as having an --/--, a12/a1 genotype and as having heterozygous alpha thalassemia trait may trigger a decision to provide genetic counseling, such as premarital counseling, to explain the risks of a child having alpha thalassemia; to treat the patient for mild anemia, or to differentially diagnose the patient as having heterozygous alpha thalassemia which can be mistaken for iron deficiency anemia or beta thalassemia. Treatments may include administration of folic acid, blood transfusions, bone marrow transplantation, stem cell transplantation, gene therapy, splenectomy, surgery to remove gallstones and treatment of secondary complications such as those resulting from a febrile episode or from infection with a microbe. A drug treatment may include administering one or more drugs such as Exjade, hydroxyurea, deferasirox, deferiprone, ferriprox, or Jadenu, Treatment with an antibiotic may include administering one or more antibiotics in the following classes of antibiotics: penicillins, tetracyclines, cephalosporins, quinolones, lincomycins, macrolides, sulfonamide, glycopeptides, aminoglycosides, or carbapenems. Treatment of yeast infections may be made using a drug in the same classes as miconazole, terconazole, or fluconazole.

Identification or characterization of a patient as having an a12/--, a12/--genotype and as having homozygous alpha thalassemia trait may trigger a decision to provide genetic counseling, such as premarital counseling, to explain the risks of a child having alpha thalassemia; to treat the patient for mild anemia, or to differentially diagnose the patient as having heterozygous alpha thalassemia which can be mistaken for iron deficiency anemia or beta thalassemia. Treatments may include administration of folic acid, blood transfusions, bone marrow transplantation, stem cell transplantation, gene therapy, splenectomy, surgery to remove gallstones and treatment of secondary complications such as those resulting from a febrile episode or from infection with a microbe. A drug treatment may include administering one or more drugs such as Exjade, hydroxyurea, deferasirox, deferiprone, ferriprox, or Jadenu, Treatment with an antibiotic may include administering one or more antibiotics in the following classes of antibiotics: penicillins, tetracyclines, cephalosporins, quinolones, lincomycins, macrolides, sulfonamide, glycopeptides, aminoglycosides, or carbapenems. Treatment of yeast infections may be made using a drug in the same classes as miconazole, terconazole, or fluconazole.

Identification or characterization of a patient as having a12/--, --/-- genotype and as having HbH disease may trigger a decision to provide genetic counseling, such as premarital counseling, to explain the risks of a child having alpha thalassemia, to treat the patient for HbH disease, or to differentially diagnose the patient from other forms of thalassemia or other conditions. Treatments may include administration of folic acid, blood transfusions, bone marrow transplantation, stem cell transplantation, gene therapy, splenectomy, surgery to remove gallstones and treatment of secondary complications such as those resulting from a febrile episode or from infection with a microbe. A drug treatment may include administering one or more drugs such as Exjade, hydroxyurea, deferasirox, deferiprone, ferriprox, or Jadenu, Treatment with an antibiotic may include administering one or more antibiotics in the following classes of antibiotics: penicillins, tetracyclines, cephalosporins, quinolones, lincomycins, macrolides, sulfonamide, glycopeptides, aminoglycosides, or carbapenems. Treatment of yeast infections may be made using a drug in the same classes as miconazole, terconazole, or fluconazole.

Identification or characterization of a patient as having a --/--, --/-- genotype and as having Bart's disease may trigger a decision to provide genetic counseling, such as premarital counseling, to explain the risks of a child having alpha thalassemia; to treat the patient HbH disease, or to differentially diagnose the patient from other forms of thalassemia or other conditions. Treatments may include intrauterine blood transfusions including those performed at an early gestational age, post-natal bone marrow transplantation or continued chronic blood transfusions, stem cell transplantation, or gene therapy. A drug treatment may include administering one or more drugs such as Exjade, hydroxyurea, deferasirox, deferiprone, ferriprox, or Jadenu, Treatment with an antibiotic may include administering one or more antibiotics in the following classes of antibiotics: penicillins, tetracyclines, cephalosporins, quinolones, lincomycins, macrolides, sulfonamide, glycopeptides, aminoglycosides, or carbapenems. Treatment of yeast infections may be made using a drug in the same classes as miconazole, terconazole, or fluconazole.

Applications. Methods according to the invention may be employed to determine whether a person has, is at risk of, is a carrier of sickle cell anemia or thalassemia, or other diseases, disorders, or conditions associated with a HBA genotype. It may be used for premarital or prenatal screening for disorders, diseases or conditions associated with abnormal expression of HBA1, HBA2 or with presence of HBA12. The method may also be used to assess the effects of genetic or pharmacological treatment of genetic diseases associated with abnormal expression of HBA1 or HBA2, or expression of HBA12, for example, after a bone marrow or other transplant of cells used to correct a genetic defect.

Multiplexing. The inventors designed many oligonucleotides for accurate PCR amplification of the HBA1, HBA2 and HBA12 genes. Oligonucleotides were evaluated for their specificity and utility for single locus PCR. Sets of primers for the multiplex PCR reaction such as those shown by FIG. 2 were selected based on melting and annealing temperature calculations for single locus PCR. These primers range in length from 18, 19, 20, 21, 22, 23, 24, 25, 26, 27, 28, 29, 30 to 31 bp. The melting temperature (Tm) of the designed primers was calculated and the Tm of each primer was maintained in the range of 59, 60, 65, 70, to 75° C. or any intermediate temperature; Tm differences between members of a primer pair was maintained at no more than 1, 2, 3, 4, or 5° C., preferably no more than 3° C.

The self-dimers or primer-dimers formations were estimated and the primers with a high level of self-dimer or primer-dimer formations were excluded. Simultaneously, the GC and the AT ratio was maintained.

The inventors confirmed the efficacy of the primers in a single locus PCR for individual amplicons of the respective genes, after which, the inventors verified all the parameters to confirm the PCR components.

After the amplification of the single locus PCR for the individual amplification of the HBA1, HBA2 and HBA12 genes separately, the most appropriate temperature for the PCR thermal profile were verified. Additionally, the most appropriate annealing temperature was tested using various types of PCR, including gradient PCR reaction. The protocol for the multiplex PCR, including the PCR mix and the thermal profiles, were adjusted to obtain the required number of PCR products. Various combinations of PCR mixtures, including bovine serum albumin, betaine and MgCl2 were tested to obtain the required PCR products in a single reaction. Thermal cycling reactions were set at various levels to have the three PCR amplicons in perfect form. The annealing temperature of the multiplexing PCR was considered very carefully based on Tm. The extension time was carefully considered to avoid the incomplete amplicon formation.

Figure 4:
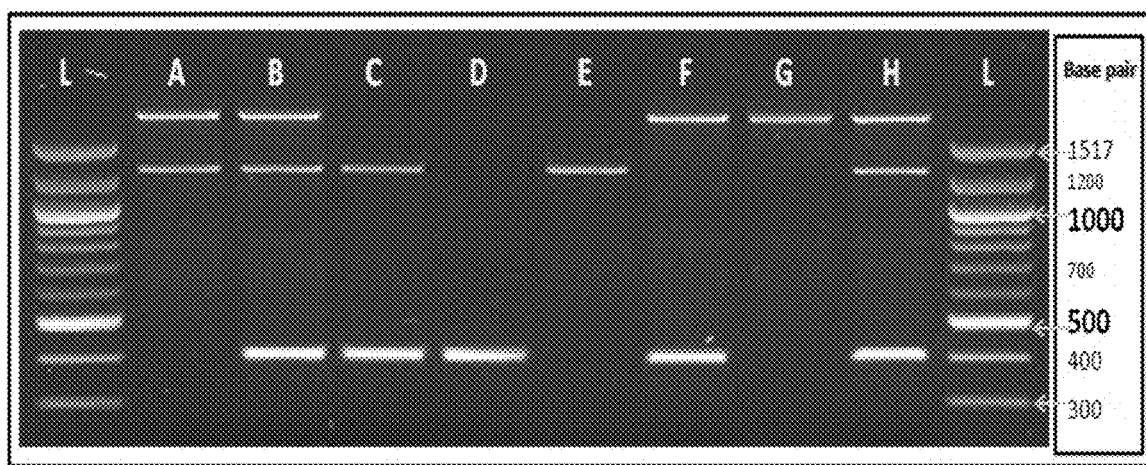
FIG. 4. Multiplex PCR and quick genotype reference guide: left and right lanes L: 100 bp Ladder; Lane A: $\alpha$1$\alpha$2/$\alpha$1$\alpha$2; Lane B: $\alpha$1$\alpha$2/$\alpha$1$\alpha$12; Lane C: $\alpha$1$\alpha$12/$\alpha$1$\alpha$12; Lane C: $\alpha$1$\alpha$12/$\alpha$1$\alpha$12; Lane D: $-\alpha$2/$-\alpha$12; Lane E: $\alpha$1-/$\alpha$1-; Lane F: $-\alpha$2/$-\alpha$12; Lane G: $-\alpha$2/$-\alpha$2; Lane H: Allelic ladder.
Figure 5:
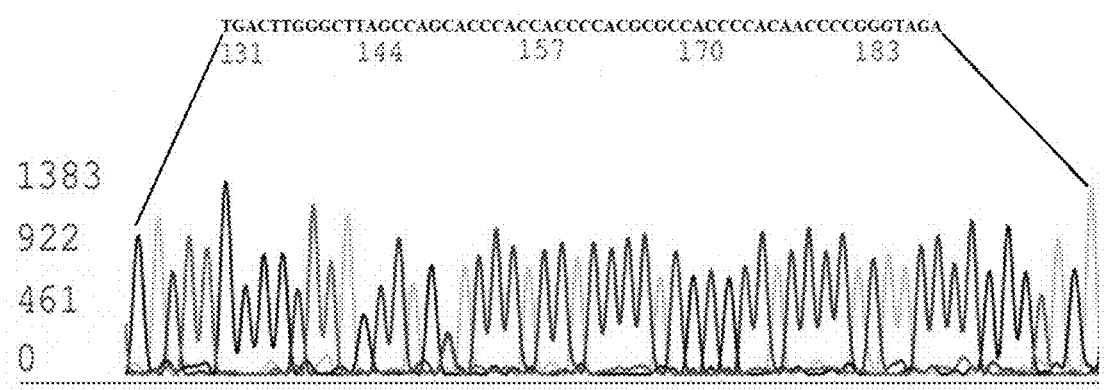
FIG. 5. A sequence electropherogram from the HBA12 gene amplicon. Sequence at top is described by SEQ ID NO: 11.

Reference guide and product confirmation. The HBA2, HBA1 and HBA12 genes have been successfully amplified simultaneously in a single PCR tube (FIG. 3) and a quick reference guide for the multiplex PCR result analysis and interpretation of these specific genotypes has been developed as shown by FIG. 4.

All the amplicons produced during the single locus PCR and the multiplex PCR were purified and confirmed by direct sequencing. All the PCR products, specifically the multiplexing products, have been gel eluted individually from the gel and purified. All the PCR products were sequenced with the respective primers (FIGS. 5-8). The sequences were compared for the origin of the amplicons and the expected region.

The inventors also confirmed that all the multiplex expected band/amplicons (1874 bp, 1231 bp and 369 bp) were of accurate length and originated from the expected regions. Two non-specific amplicons between the regions 1874 bp and 1231 bp, which were 1517 and 1550 bp in length, respectively (FIG. 3) were identified. These two non-specific amplicons were not used in the interpretation of the multiplex results; rather the allelic ladder was used for comparison and interpretation.

EXAMPLES

The following examples illustrate various aspects of the present invention. They are not to be construed to limit the claims in any manner whatsoever.

Example 1

Designing of Specific Primers for HBA1, HBA2 and HBA12

HBA1, HBA2 and HBA12 genes were sequenced and used to design the specific primers for the amplification of these genes in samples obtained from the Saudi population, see FIG. 1. The primers for the amplification of these three genes were designed specifically for each gene. All the primers have been designed with the sequence length from 24 to 31 bp nucleotides. All the manually designed primers were subjected for the possible primer-primer dimer or interactions. National Center for Biotechnology Information (NCBI) tool and Basic Local Alignment Search Tool (PRIMER-BLAST) were used to identify the specificity and the possible amplification of the non-specific amplicon.

Example 2

Single Locus Polymerase Chain Reaction

A simple PCR procedure for the amplification of individual alpha globin genes was standardized. Each set of primers was thoroughly checked for the accurate amplification of specific amplicons without amplification of any nonspecific amplicons. The inventors standardized the individual PCR with the annealing temperature ranging from 65-68° C. to make the primers suitable for multiplexing.

The amplification of the individual PCR products was carried out at volume of 25 µL of reaction: 1× Top Taq Buffer; 10 µM Reverse primer; 10 µM Forward primer; Q-reagent; 25 mM dNTP; 2.5 U Top Taq DNA polymerase; and 25 ng/µl DNA Template. Temperature profile: 94° C.-5 mins; 35 cycles of 94° C.-30 seconds, Annealing temperature 57-67/30 seconds; 72° C./0.5 to 2 mins and final extension 72° C.-10 mins.

Example 3

Multiplex PCR

A pool of oligonucleotides (FIG. 2) was selected for the simultaneous multiplex PCR amplification of HBA, HBA2 and HBA12 genes in a single PCR tube. The PCR recipe in a total volume 50 µl for the multiplex amplification of HBA1, HBA2 and HBA12 genes was PCR 10× Buffer-5.0 µl; Q-Reagent-10 µl; 10 mM dNTPs-1.0 µl; 2.5 U Top Taq DNA polymerase-0.3 µl; 10 µM primers such as, Ma12F—0.5 µl; Ma2R—2.0 µl; Ma2F—2.0 µl; Ma12R—1.5 µl; Ma1F—1.5 µl; 25 ng/µl Sample DNA-2.0 µl and nuclease free distilled water-24.2 µl.

The PCR thermal profile for the amplification for the HBA1, HBA2 and HBA12 genes in a single PCR tube is shown below.
Step 1: Initial denaturation at 95° C. for 3 mins.
Step 2: Denaturation at 95° C. for 30 secs.
Step 3: Annealing at 69° C. for 1 min. 30 secs.
Step 4: Extension at 72° C. for 2 mins. 15 secs.
Step 5: Repeat: Go to Step 2, 30 cycles.
Step 6: Final Extension at 72° C. for 5 mins.
Step 7: Store at 4° C.

The above protocol was verified using thermal cyclers from various manufacturers including those available from BioRad, Biometra and Eppendorf.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

---

The invention claimed is:

1. A method for treating a subject at risk of a hemoglobin A (HBA) associated disease or trait by detecting Hemoglobin alpha 1 (HBA1) gene, Hemoglobin alpha 2 (HBA2) gene, and Hemoglobin alpha 12 (HBA12) genes in the subject, comprising:
obtaining a sample from the subject;
contacting the sample with at least one set of primers for each of HBA1, HBA2 and HBA12 under conditions suitable for the primer sets to amplify DNA in the sample by multiplex polymerase chain reaction (PCR), wherein the set of HBA1 primers are MA1F (SEQ ID NO: 3) and MA12R (SEQ ID NO: 4), the set of HBA2 primers are MA2F (SEQ ID NO: 5) and MA2R (SEQ ID NO: 2 or 6) and the set of HBA12 primers are MA12F (SEQ ID NO: 1) and MA2R (SEQ ID NO: 2 or 6),
detecting the presence of, or levels of, HBA1, HBA2 and HBA12 DNA amplified by each primer set, thereby detecting a genotype of the subject, and
treating a course of an HBA-associated disease or treating a trait using a detected genotype in combination with clinical data to inform a treatment decision.

2. The method of claim 1, wherein said subject carries gene conversion HBA12.

3. The method of claim 1, wherein said subject does not carry gene conversion HBA12.

4. The method of claim 1, wherein the sample is blood, plasma or serum, or white blood cells, or cells obtained from a buccal swab.

5. The method of claim 1, wherein the sample is cells obtained from a buccal swab.

6. The method of claim 1, wherein the primers for HBA1, HBA2 and HBA12 are part of a single primer pool.

7. The method of claim 1, further comprising identifying the subject as being at risk of sickle cell disease when the presence of amplified HBA1, HBA2 and HBA12 is detected.

8. The method of claim 1, further comprising identifying the subject as having sickle cell trait or sickle cell disease when the presence of amplified HBA1, HBA2 and HBA12 is detected.

9. The method of claim 1, further comprising identifying the subject as being at risk of sickle cell disease when the presence of amplified HBA1, HBA2 and HBA12 is detected and treating the subject for sickle cell disease with at least one of penicillin, hydroxyurea, a transfusion of red blood cells, or by hematopoietic stem cell transplantation.

10. The method of claim 1, further comprising identifying the subject as being at risk of thalassemia when the presence of amplified HBA1, HBA2 and HBA12 is detected.

11. The method of claim 1, further comprising identifying the subject as being at risk of thalassemia when the presence of amplified HBA1, HBA2 and HBA12 is detected and treating the subject for thalassemia with at least one of a blood transfusion, iron chelation therapy, or folic acid.

12. A method for genetic counselling comprising the method of claim 1, wherein said treating a course of an HBA-associated disease or trait using the detected genotype in combination with clinical data comprises informing the subject of his or her HBA-associated gene associations.

13. The method of claim 12, wherein said genetic counseling is premarital counseling.

14. The method of claim 12, wherein said subject is identified as having an a12/a1, a12/a1 genotype.

15. The method of claim 12, wherein said subject is identified as having an a12/a1, a12/-- genotype.

16. The method of claim 12, wherein said subject is identified as having an a12/--, a12/-- genotype.

17. The method of claim 12, wherein said subject is identified as having an a12/--, --/-- genotype or a --/--, --/-- genotype.

18. A method for differential diagnosis comprising the method of claim 1, wherein said treating a course of an HBA-associated disease or trait using the detected genotype in combination with clinical data comprises informing a health care provider of the subject's HBA-associated gene associations with sickle cell disease or with thalassemia.

19. The method of claim 18, wherein said subject carries gene conversion HBA12.

20. The method of claim 18, wherein said subject does not carry gene conversion HBA12.

* * * * *